| United States Patent [19] | [11] Patent Number: 4,870,105 |
| Fordtran | [45] Date of Patent: Sep. 26, 1989 |

[54] PHOSPHORUS BINDER

[75] Inventor: John S. Fordtran, Dallas, Tex.

[73] Assignee: Braintree Laboratories, Inc., Braintree, Mass.

[21] Appl. No.: 35,341

[22] Filed: Apr. 7, 1987

[51] Int. Cl.$^4$ ............................................. A61K 31/19
[52] U.S. Cl. .................................................... 514/557
[58] Field of Search ......................................... 514/557

[56] References Cited

PUBLICATIONS

Chemical Abstracts, vol. 52, col. 3277a (1958).
Chemical Abstracts, vol. 57, col. 12976c (1962).
PDR, 26th Ed., p. 683.
Chemical Abstracts, vol. 57, col. 3277c (1962).
Calcium Acetate Use in the Body, NERAC Retrospective Search, U.S. Patent Bibliographic Data Base, Run dtd. 02/04/87.
Calcium Acetate Use in the Body, NERAC Retrospective Search, CA Search-Biochem., Run dtd. 02/05/87.
Phosphorous Absorption in the Body, NERAC Retrospective Search, USG/NTIS, Run dtd. 02/06/87.
Phosphorous Absorption in the Body, NERAC Retrospective Search, Life Sciences Collection, Run dtd. 02/07/87.
Phosphorous Absorption in the Body, NERAC Retrospective Search, NASA, Run dtd. 02/08/87.
Phosphorous Absorption in the Body, NERAC Retrospective Search, CA Search-Biochem., Run dtd. 02/09/87.

Primary Examiner—Frederick E. Waddell
Attorney, Agent, or Firm—Lorusso & Loud

[57] ABSTRACT

A composition for oral administration to an individual for the purpose of inhibiting gastrointestinal absorption of phosphorous, which includes calcium acetate. A method of inhibiting gastrointestinal absorption of phosphorous, comprising administering orally the composition, preferably close in time to food and beverage consumption.

8 Claims, No Drawings

PHOSPHORUS BINDER

BACKGROUND

In chronic renal failure, phosphorus retention plays a major role in the development of secondary hyperparathyroidism and osteodystrophy. Bricker, N. S. et al., *Archives of Internal Medicine,* 123: 543-553 (1969); Rubini, M. E. et al., *Archives of Internal Medicine,* 124:663-669 (1969); Slatopolsky, E. et al., *Journal of Clinical Investigation,* 50: 492-499 (1971); Bricker, N. S., *New England Journal of Medicine,* 286: 1093-1099 (1972); Slatopolsky, E. S. et al., *Kidney Int.,* 2: 147-151 (1972).

To prevent phosphorus retention, antacids are often used to bind dietary phosphorus and, thus, prevent its absorption. The process, referred to as phosphorus binding, appears to be a chemical reaction between dietary phosphorus and the cation present in the binder compound, resulting in the formation of insoluble and hence unabsorbable phosphate compounds, adsorption of phosphorus ions on the surface of binder particles, or a combination of both. The cation in some antacids is aluminum or calcium.

Presently-used antacids are, however, quite inefficient at binding phosphorus in vivo. For example, in a recent study by Ramirez, et al., it was noted that even though aluminum- or calcium-containing antacids were administered in large excess, they bound only 19-35 percent of dietary phosphorus. Ramirez, J. A., et al., *Kidney Int.,* 30: 753-759 1986). Similar conclusions can be derived from data presented in earlier studies. Kirsner, J. B. *Journal of Clinical Investigation,* 22: 47-52 (1943); Clarkson, E. M. et al., *Clinical Science,* 43: 519-531 (1972); Cam, J. M. et al., *Clinical Science and Molecular Medicine,* 51: 407-414 (1976); Man, N. K. et al., *Proceedings of the European Dialysis and Transplantation Association,* 12: 245-55 (1975).

Antacids are also used widely, often in large quantities, for indigestion, heartburn or peptic ulcer disease. Despite their consumption in large amounts and often over long periods of time, however, phosphorus depletion is uncommon in these settings. This fact is additional evidence of the inefficiency of antacids as phosphorus binding agents.

The inefficiency of commonly used phosphorus binders creates a clinical dilemma: the dose of the binder must be increased to control hyperphosphatemia, but increased risk of toxicity of the binder results. This includes bone disease and aluminum dementia from aluminum-containing antacids and hypercalcemia and soft tissue calcification from calcium-containing antacids. These risks are particularly problematic in patients with chronic renal disease. It would be very useful to have a phosphorus binder available, which does not have the risks associated with ingestion of presently-available binders and which is more efficient in binding phosphorus and, thus, does not have to be consumed in the large quantities necessary, for example, when calcium carbonate-containing compositions are used. Such a phosphorus binder would be particularly valuable for administration to individuals with chronic renal failure, in whom phosphorus retention is a serious concern and the risk of toxicity from consumption of presently-available binders is greater than in individuals in whom kidney function is normal.

DISCLOSURE OF THE INVENTION

The present invention relates to a method of binding phosphorus in the gastrointestinal tract and, thus, reducing phosphorus absorption from the intestine. It also relates to a method of reducing serum phosphate levels, since phosphorus is bound in the gastrointestinal tract, resulting in lower phosphorus absorption than would otherwise occur. It is particularly useful in the treatment and prevention of hyperphosphatemia in individuals with renal disease, or other disease, in which the ability to excrete phosphorus from the body (e.g., in the urine) is impaired.

The method of the present invention comprises administering orally to an individual a composition which includes calcium acetate in sufficient quantity to effectively bind phosphorus present in food and beverages consumed by the individual and, thus, prevent its absorption in the intestine. Administration of calcium acetate according to the method of the present invention is also associated with lower calcium absorption and fewer side effects than is evident with administration of presently-available phosphorus binders.

DETAILED DESCRIPTION OF THE INVENTION

The present invention relates to a composition for oral administration to an individual, which comprises calcium acetate and is useful in reducing phosphorus absorption in the gastrointestinal tract. Calcium acetate has been shown to be effective in inhibiting phosphorus absorption, when administered orally to individuals, and has been shown to prevent the absorption of ingested phosphorus to a greater extent than other calcium-containing binders. As a result, calcium acetate, alone or in combination with other materials, can be used to bind phosphorus in the gastrointestinal tract, thus reducing the percentage of an amount of phosphorus consumed (i.e., of a given "dose" of phosphorus) which is absorbed. It has also been shown that when calcium acetate is administered close in time to food consumption, it is associated with lower calcium absorption than occurs when other calcium-containing compounds are used.

The present invention also relates to a method of inhibiting gastrointestinal phosphorus absorption. The method of the present invention is based on the demonstration that calcium acetate is an effective binder of phosphorus when administered orally to an individual. In addition, use of the method of the present invention has been shown to be associated with lower calcium absorption than has administration of other calcium compounds, when calcium acetate is consumed at (or in close proximity to) the time at which foods and beverages are consumed.

As a result, it is possible to administer calcium acetate to reduce absorption of dietary phosphorus, which has the net effect of reducing the risks of adverse effects (e.g., bone disease and secondary hyperparathyroidism) observed in individuals (e.g., chronic renal patients) in whom the ability to excrete phosphorus in the urine is impaired. As used herein, the term phosphorus includes phosphorus and phosphate in its various forms (e.g. $HPO_4^-$, $PO_4^{-3}$, etc.) Because calcium acetate intake at the time foods or beverages are consumed is associated with lower calcium absorption than observed with consumption of other calcium-containing compounds, it provides the additional advantage of reduced risk of adverse effects (e.g., calcium deposits in soft tissues) evident when increased quantities of calcium are absorbed.

According to the method of the present invention, calcium acetate is administered, alone or in combination with other substances (e.g., gelatin, in a hard gelatin capsule; materials necessary to form a tablet or caplet as a delivery vehicle for the calcium acetate; a second phosphorus binder) in sufficient quantities to reduce phosphorus absorption in the gastrointestinal tract. The calcium acetate is administered orally, preferably close in time to food and beverage consumption. In one embodiment, 1-2 grams of anhydrous calcium acetate (12.5-25 milliequivalents calcium) is taken prior to food consumption (e.g., meal time) and a second dose of 1-2 grams of anhydrous calcium acetate is taken after food consumption. The dose or quantity to be taken at a given time varies on an individual-by-individual basis and can be adjusted as needed (e.g., by monitoring serum concentration of phosphorus and calcium).

It has been determined, through calculations and in vitro assays, that calcium acetate is a more effective phosphorus binder (i.e., it binds a greater percent of a given quantity of phosphorus) than other calcium compounds. This has been verified by in vivo assessment of the phosphorus-binding ability of calcium acetate, which provides clear evidence that calcium acetate, when administered orally to an individual, is effective in inhibiting phosphorus absorption in the individual.

Theoretical Calculations of Phosphorus Binding

Equilibrium constant expressions for the chemical reactions involved in the interaction of phosphorus and binders were used to calculate theoretical binding of phosphorus by aluminum-, calcium- and magnesium-containing compounds. Calculations were done to estimate phosphorus binding at equilibrium, at different pH levels, for the three types of compounds. This work is described in detail in Example I.

In Vitro Methods

To assess the relative phosphorus-binding capability of compounds, in vitro procedures were used. In these procedures, a phosphorus solution was mixed with the antacid or compound to be tested ('the binder'). After incubation periods of varying lengths, the mixture was filtered. The decrease in the amount of phosphorus in the filtrate (i.e., difference between the amount initially present in the solution as mixed and that present in the filtrate) represented the amount of bound phosphorus. This amount was expressed as a percent of the total phosphorus present in the original solution. Assays were stopped when 100% phosphorus binding was achieved, or no more than 5% increase in phosphorus binding was observed in a 6-7 day period of further incubation.

In these procedures, 320 mg of elemental phosphorus ($NaH_2PO_4 \cdot H_2O$, equal to 10-31 mEq of phosphate, depending upon pH) and binder (antacid or other compound being tested) containing 75 mEq of calcium, magnesium or aluminum were used. This choice was based on the fact that these amounts are the same as the phosphorus content of a test meal and the dose of binder used in an in vivo study by Ramirez and co-workers. Ramirez, J. A., et al. *Kidney Int.*, 30: 753-759 1986). Table 1 lists the compounds tested as phosphorus binders, as well as an indication of their published water solubilities. Linke, W. F. (ed.), *Solubilities: Inorganic and metal-organic compounds* (4th Edition), (1965); Weast, R. C. (ed.), *CRC Handbook of Chemistry and Physics* (65th Edition), (1984-85). Except as specified in the footnote to the table, all compounds used were of reagent grade.

TABLE 1

BINDERS TESTED AND THEIR SOLUBILITIES

| BINDERS | SOLUBILITY gm/100 ml of water | temp (°C.) |
|---|---|---|
| Calcium chloride dihydrate | 56.0 | 38.5 |
| Calcium acetate monohydrate | 43.6 | 0 |
| Calcium lactate | 7.9 | 30 |
| Calcium gluconate | 3.85 | 25 |
| Calcium citrate | $9.6 \times 10^{-2}$ | 25 |
| Calcium carbonate | $5.6 \times 10^{-3}$ | 25 |
| Aluminum chloride hexahydrate | 31.1 | 25 |
| Aluminum hydroxide powder | $7.8 \times 10^{-9}$ | 25 |
| Amphojel (aluminum hydroxide gel)§ | Unknown | |
| Basaljel (aluminum carbonate gel)§ | Unknown | |
| Sucralfate* | 0.1 | 20 |
| Magnesium hydroxide | $6.4 \times 10^{-4}$ | 25 |

§Wyeth Laboratories, Philadelphia, PA
*Carafate, Marion Laboratories, Kansas City, MO. Solubility value from the manufacturer.

In these experiments, the effect of binder dose was also assessed by varying the amount of binder used (i.e., it was halved or doubled, to 38 or 150 meq of binder), while the amount of phosphorus content was kept constant. This work is described in detail in Example II.

The work described above and in Examples I and II serves as the basis for understanding factors which determine the degree to which phoshorus reacts chemically with compounds (binders) which are used to reduce dietary phosphorus absorption in the intestine. As explained, the first step was calculation of the degree to which various compounds are theoretically capable of binding phosphorus at equilibrium at varying pH levels. These calculations were based on equilibrium constants available in the literature. In the second step, in vitro experiments were conducted to verify results of these calculations and to determine the time required to reach equilibrium.

This comparison showed that in all cases except aluminum hydroxide powder, there was good general agreement between equilibrium values calculated on theoretical grounds and equilibrium values achieved in vitro. In vitro, aluminum hydroxide powder bound considerably less phosphorus than expected, based on theoretical equilibrium values. This may be due to the fact aluminum hydroxide is extremely insoluble (Table 1). For calcium compounds (other than calcium citrate) and magnesium hydroxide, the in vitro equilibrium values were somewhat lower than expected, based on the theoretical equilibrium values, in the lower pH range. There are several possible explanations for this discrepancy, including the possibility that equilibrium had not been established in vitro in the time allowed; or that the theoretical calculations are overestimated because of the assumption of zero ionic strengths; the possible underestimation of the competition by $H^+$ (e.g., overestimating the binding) in the lower pH range because the equilibrium constants used in calculations might have been obtained under different experimental conditions; and the occurrence of a pH drift over time and the marked influence of pH on binding in this range. The small discrepancy does not, however, significantly affect an analysis of the data to identify factors important in governing phosphorus binding.

Factors Which Affect Binding at Equilibrium

Results of calculations which take into account the equilibrium constants for the reactions between binder cation and phosphates, between H+ and phosphates, and between binder cation (calcium) and competing anion (citrate) were used to identify factors which affect phosphorus binding at equilibrium. This analysis showed that binding at equilibrium depends upon the binder used, pH, presence of competing anions and the relative amounts of binder and phosphorus, which is relative to solubility.

In Vivo Phosphorus Binding

Assessment of the ability of calcium acetate to inhibit phosphorus absorption in humans was also carried out. This work is described in detail in Example III.

Briefly, the assessment was carried out as follows: One of three calcium-containing compounds (referred to as phosphorus binders) was administered orally at meal time in ten subjects. The subjects were fed a test meal of known amounts of phosphorus and calcium. The ability of calcium acetate to inhibit phosphorus absorption was assessed and compared with the ability of other calcium compounds, such as calcium carbonate and calcium citrate, to inhibit phosphorus absorption. A placebo (lactose) was administered orally on a separate occasion.

Total phosphorus and total calcium absorption were measured; results are shown in Tables 2 and 3, respectively. When the placebo was consumed, mean phosphorus absorption was 77 percent (percent of total phosphorus ingested) and mean calcium absorption was 19 percent (percent of total calcium ingested). Mean percent absorption of phosphorus and calcium when the three calcium-containing compounds were consumed are as follows:

|                    | Phosphorus | Calcium |
|--------------------|------------|---------|
| Calcium acetate    | 26         | 16      |
| Calcium carbonate  | 44         | 25      |
| Calcium citrate    | 49         | 22      |

Individual results are shown in Tables 2 and 3 (Example III).

Thus, when calcium acetate was consumed, mean percent phosphorus absorbed was significantly lower ($p<0.001$) than when calcium carbonate or calcium citrate was consumed. This was also the case for mean percent calcium absorption ($p<0.05$).

This study showed the effect of ingestion of calcium at the time of food and beverage consumption. This effect is referred to as phosphorus binding, which, in vivo, is defined as the degree to which phosphorus absorption is inhibited by a phosphorus binder. (In the in vitro experiments, binding is defined as the extent of phosphorus precipitation/adsorption.) For binding agents to be effective in vivo, they must interfere with phosphorus absorption, by precipitating or adsorbing or otherwise "tieing up" phosphorus so that it cannot be absorbed in the gastrointestinal tract. In rats and chicks, phosphorus absorption has been shown to occur almost exclusively in the small intesting. Cramer, C. F. et al., *Canadian Journal of Biochemistry and Physiology,* 39:499–503 (1961). Hurwitz, S. et al., *American Journal of Physiology* 39:499–503 (1961). In humans, phosphorus absorption is also thought to occur mainly in the small intestine. Read, N. W., et al., *Gastroenterology,* 70:1276–1282 (1980). Assuming that no colonic absorption of phosphorus occurs, a binder must dissolve and react with phosphorus within 4–6 hours, if it is to be effective in vivo. The most efficient place for binding to occur would be the stomach, before phosphorus is exposed to absorption sites in the small intestine. In the small intestine, phosphorus absorption processes will compete with the binder for the phosphorus. Absorption of the binder itself will result in its removal from the gut lumen (making less available to bind with phosphorus).

Within the gut there are wide changes in pH. pH of homogenized meals used in various studies has been about 5. Slatopolsky E. S. et al., *Kidney Int.* 2:147–151 (1972). Fordtran, J. S. et al., *American Journal of Digestive Diseases,* 11:503–521 (1966); Ramirez, J. A. et al., *Kidney Int.,* 30: 753–759 (1986). As a result of acid secretion, the pH of stomach contents drops to 2–3; in the upper small intestine it increases to about 4–6, and in the lower intestine to as high as 7–8. Fordtran, J. S. et al., *American Journal of Digestive Diseases,* 11:503–521 (1966). Antacids (like Amphojel and calcium carbonate) raise pH in the stomach, but generally not above pH 3–4. Deering, T. B. et al., *Gastroenterology,* 73:11–14 (1977). These pH changes can have several important effects on phosphorus binding. Low pH (from gastric acid, food, or acid microclimate of small intestine) would help dissolve poorly water soluble compounds. This would facilitate the binding reaction if binding is possible at low pH (e.g., as is the case with aluminum compounds). Calcium-containing compounds cannot bind phosphorus when pH is 3 or less and would bind little phosphorus in the stomach. However, if solubilized, calcium compounds can bind phosphorus quickly in the higher pH of the small intestine. Thus, the changes in pH can have complex and sometimes opposing effects on phosphorus binding.

Calcium acetate has, through the work described above and in Example III, been shown to be an effective phosphorus binder in the gastrointestinal tract and, as a result, able to reduce phosphorus absorption. This is because it is more soluble than other binders (Table 1), thus making more calcium available for binding to phosphate and preventing phosphate absorption. Similarly, because the calcium is complexed with phosphate, the ingested dose of calcium is not available for absorption either. This explains why calcium acetate results in both lower phosphorus and lower calcium absorption than the other binders.

EXAMPLE I

Theoretical Calculation of Phosphorus Binding

Using equilibrium constant expressions for the chemical reactions involved in the interaction of phosphorus and binders used, theoretical binding at equilibrium under the conditions used was calculated. The binding reaction was the precipitation reaction of either $PO_4^{3-}$ or $HPO_4^{2-}$ with a metal ion, the metal ion binders being present in excess. Maximum binding was estimated by calculating the total phosphate which could be present in a saturated solution of the metal phosphate precipitate in the presence of excess metal binder at the selected pH. For a binding reaction of the form:

$$aM + bP \rightleftharpoons M_aP_b(s)$$

(where M=metal binder, P=$PO_4^{3-}$ or $HPO_4^{2-}$, s=solid or precipitate form, a=moles of M, b=moles of P), the concentration at equilibrium was assumed to be governed by the expression:

$$K = [M]^a[P]^b,$$

where [ ] denotes molar concentration of the saturated solution and K is the solubility product for the binding reaction. Total phosphate concentration was obtained by simultaneous solution of the binding reaction equilibrium constant expression and the expressions governing the relative amounts of inorganic phosphate species ($H_3PO_4$, $H_2PO_4^-$, $HPO_4^{2-}$, $PO_4^{3-}$). In cases where the metal formed soluble complexes with other species in solution, such as citrate, equilibrium constants for these were also considered in determining total phosphate. In all cases, the ionic strengths were assumed to be zero and activity coefficients to be unity. Because of these assumptions, the calculations might slightly overestimate binding. The binding of phosphorus by calcium chloride was estimated, using the method described above. Similar calculations were made for phosphorus binding by the other compounds used. Initial total phosphate concentration was 0.0172M (or 320 mg/600 ml) and initial calcium ion ($Ca^{2+}$) concentration was 0.0625M (or 1500 mg/600 ml). The concentration of various forms of phosphate at pH 4 was calculated, using the equilibrium constant expression governing the hydrogen-phosphate equilibra. Sillen L. G. et al., *The Chemical Society*, London (1964). At pH 4, the dominant form of phosphate is $H_2PO_4^-$. Using these concentrations and the equilibrium constant expression for the precipitation of $CaHPO_4$ and $Ca_3(PO_4)_2$, it was determined that only $CaHPO_4$ would precipitate. The following reactions occur at equilibrium:

$$CaHPO_4(s) \rightleftharpoons Ca^{2+} + HPO_4^{2-} \quad K = 4 \times 10^{-7} \quad (1)$$

$$HPO_4^{2-} + H^+ \rightleftharpoons H_2PO_4^- \quad K = 1.47 \times 10^7 \quad (2)$$

Combining equations 1 and 2:

$$CaHPO_4(s) + H^+ \rightleftharpoons Ca^{2+} + H_2PO_4^- \quad K = 5.9 \quad (3)$$

or $$\frac{[Ca^{2+}][H_2PO_4^-]}{[H^+]} = 5.9 \quad (4)$$

If all the phosphate (0.0172M) were to precipitate as $CaHPO_4$, it would leave (0.0625 −0.0172) M of calcium in solution. If precipitation were not 100%, an additional amount, x M of calcium and phosphate, would be in solution. Hence at equilibrium:

$$[H_2PO_4^-] = x$$

and $[Ca^{2+}] = (0.625-0.0172)+x$

Substituting these values in equation 4:

$$x = 0.0105 \text{ M, at pH} = 4.$$

Thus phosphate in precipitate = 0.0172 − x
 = 0.0172 − 0.0105
 = 0.0067 M

Thus percent binding

= $\frac{\text{phosphate in precipitate}}{\text{total phosphate}} \times 100$

= $\frac{0.0067}{0.0172} \times 100$

= 38.9%

Calculations were done to estimate binding at equilibrium at different pH levels for aluminum, calcium and magnesium compounds. Based on these determinations, it appears that aluminum compounds should bind 100% of the phosphorus in pH range 3.5–7.5. Above pH 7.5, binding would drop (e.g. to 96% at pH 8) because of precipitation of aluminum hydroxide ($Al(OH)_3$) For calcium compounds (except calcium citrate) and for magnesium compounds, binding is estimated to be about 100% at pH levels above 5.5 and 6.0, respectively. Binding appears to drop to 0% at pH 3.5 for calcium compounds (except calcium citrate) and to 0% at pH 4.0 for magnesium compounds. The reason for this appears to be the fact that at low pH, hydrogen ion concentration ([$H^+$]) increases; $H^+$ competes for phosphorus more effectively than does calcium or magnesium. In contrast, at low pH aluminum competes effectively with $H^+$, with the result that there is 100% binding). At pH less than 5.5, it is estimated that calcium would bind phosphorus more effectively than would magnesium. Thus, based on these calculations, at pH less than 6, the theoretical order of phosphorus binding (excluding calcium citrate) is $Al^{3+} > H^+ > Ca^{2+} > Mg^{2+}$.

In contrast to anions of the other calcium compounds used in these experiments, citrate forms soluble complexes with calcium, reducing the availability of calcium for reaction with phosphorus. Walser, M., *Journal of Physical Chemistry*, 65: 159 (1961). This effect is particularly evident at low pH.

In addition to the calculations which were carried out for 75 mEq. of binder cation, calculations were carried out for the same compounds at three other concentrations: 150, 38 and 19 mEq. A two-fold increase (i.e., to 150 mEq.) or a reduction by one half (i.e., to 38 mEq.) in calcium-containing binders (other than calcium citrate) would not change equilibrium phosphorus binding at pH greater than 6. At pH less than 6, an increase in binder results in increased binding. As also shown, however, reducing the amount of binder to one quarter of the original amount (i.e., to 19 mEq.) reduces phosphorus binding from 100% to 60% at pH greater than 6.

Similar calculations for aluminum compounds showed that binding at pH 3.5–7.5 would be 100% when 150, 75, or 38 mEq aluminum is used; with 19 mEq, binding would drop to 61%.

EXAMPLE II

Observed In Vitro Phosphorus Binding

In vitro experiments were carried out in an effort to evaluate the time required to reach equilibrium with different binder compounds to determine the extent to which observed in vitro binding agrees with theoretically calculated binding.

In this work, 320 mg. of elemental phosphorus ($NaH_2PO_4 \cdot H_2O$, equal to 10–31 meq. phosphate, depending on pH) and binder (antacid or other compound being tested) containing 75 mEq. of calcium, aluminum or magnesium were used.

For each binder study conducted, phosphorus solutions containing 320 mg. of elemental phosphorus were titrated by addition of hydrogen chloride (HCl) or sodium hydroxide (NaOH), to one of four initial pH levels: 4, 5, 6 and 7. Drift in pH occurred over time and the solutions were retitrated to their initial pH immediately after addition of the binder solution and at 1 and 24 hours after binder addition. If experiments were extended for longer periods, the solutions were also retitrated to their initial pH at four days and at one, two and three weeks. pH drift was large when calcium carbonate, magnesium hydroxide and Basaljel were used as phosphorus binders and additional experiments for these compounds were done at pH 4 and 5, using an autotitrator.

EXPERIMENTAL PROCEDURE

The following procedure was used to assess the relative binding capability of each compound: 1.43 g of $NaH_2PO_4 \cdot H_2O$ (320 mg of elemental phosphorus) were dissolved in 570 ml of deionized water. The binder was dissolved (or suspended, in the case of insoluble compounds) in deionized water, to a volume of 30 ml.

The binder solution or suspension was added to the phosphorus solution to produce a final volume of 600 ml (the volume of the homogenized meal used in the in vivo study by Ramirez and co-workers described above). Each mixture was stirred with a magnetic stirrer, during titration with HCl or NaOH, at approximately 100 revolutions per minute for approximately one minute. Beakers containing the resulting solutions were kept (covered) in a shaker bath at 37° C., with shaking at approximately 20 cycles per minute. In those cases in which an autotitrator was used, the beakers were kept at room temperature, and mixtures were stirred with a magnetic stirrer at approximately 100 revolutions per minute. Samples for phosphorus assay were taken from the solutions just prior to retitration to the initial pH at one and 24 hours after binder was added; in some cases, samples were also removed at one, two and three weeks after addition of binder to phosphorus solution. In the case of calcium carbonate, additional samples were obtained at 4 hours after addition of the binder. Samples were centrifuged at 3000 g for 30 minutes. The supernatant was filtered sequentially through Whatman #50 filter paper and then through a 0.2 micron millipore filter before analysis. Preliminary experiments had demonstrated that the filtration process had no effect on the phosphorus concentration of solutions having known phosphorus concentration. Phosphorus was assayed by the method of Fiske and Subbarow. Fiske, C. H. and Y. Subbarow, *Journal of Biological Chemistry*, 66: 375–400 (1925).

Calcium Compounds

Such experiments were carried out using calcium-containing binders. Results at 1 and 24 hours were similar to each other and to the theoretically calculated binding at equilibrium, indicating that equilibrium is quickly approached. Calcium chloride, calcium lactate and calcium gluconate show a similar pH effect, although calcium lactate and calcium gluconate approach equilibrium more slowly.

Phosphorus binding with calcium carbonate varied with pH. Calcium carbonate bound 10% to 25% (of total amount of phosphorus added) at one hour, 8% to 80% at 4 hours and 6% to 93% at 24 hours. At one week, binding approached theoretical equilibrium values at all pH levels tested. At 4 and 24 hours, binding is much closer to equilibrium values at lower pH (4–5.5) than it is at higher pH (6.5–7.5). As shown in Table 1, calcium carbonate is poorly soluble in water. Earlier establishment of equilibrium at low pH (where calcium carbonate is more soluble), and later establishment of equilibrium at higher pH (where calcium carbonate is less soluble), suggests that slow dissolution of poorly soluble compounds is one factor controlling the rate at which the phosphorus binding reaction reaches equilibrium.

Calcium citrate was the least effective calcium salt tested. In the lower pH range, it binds very little phosphorus (as expected from calculated equilibrium values); at pH greater than 6.5, binding increases gradually to 53% by one week, thus approaching the calculated equilibrium value.

Bonferroni multiple comparisons were used to compare phosphorus binding by different compounds at one hour. Miller Jr., R. P. (ed.), *Simultaneous Statistical Inference*, (2nd Edition), Springer-Verlaz, New York, pp. 67–70, (1981). The following statistically significant (P 0.05) differences were evident:

Calcium acetate or Calcium chloride > Calcium lactate or

Calcium gluconate > Calcium carbonate > Calcium citrate

Aluminum Compounds

Experiments were also carried out using aluminum-containing compounds. Aluminum chloride binds virtually 100% of phosphorus within one hour, showing that equilibrium is established quickly. In contrast, aluminum hydroxide powder binds very little phosphorus at hour; no increase in binding occurs over time, up to 1 week. Poor solubility may be the reason for this poor binding (Table 1). Results for aluminum hydroxide gel (Amphojel) and aluminum carbonate gel (Basaljel) were similar. They bind approximately 40–65% phosphorus at 1 hour, with binding being greater in lower pH range. A progressive increase in phosphorus binding with time is seen: the calculated equilibrium value of 100% is approached between 24 hours and 1 week at pH 4–5 and in 3 weeks at pH 6–7. Binding with sucralfate at 1 and 24 hours is significantly better than that observed with Amphojel and Basaljel, based on Bonferroni multiple comparisons. It approaches theoretical equilibrium values at 1 week.

Magnesium Compounds

Similarly, in vitro experiments were carried out using magnesium-containing compounds. Theoretical equilibrium values for magnesium hydroxide (a poorly-soluble compound - Table 1) were approached at two weeks.

'Dose Response' Experiments

"Dose-response" experiments, were also carried out. In this work, three different amounts (38, 75 and 150 mEq) of calcium acetate, calcium carbonate and Amphojel and a constant amount of phosphorus were used. Phosphorus binding was determined at one hour after addition of the binder. Progressive binding occurs with increasing amounts of binder. This effect is most marked with Amphojel, for which equilibrium is approached in 24 hours, when 150 mEq. of Amphojel are used and in 3 weeks, when a 75 mEq. dose is used.

EXAMPLE III

In vivo assessment of phosphorus and calcium binding

In vivo phosphorus binding by calcium acetate, calcium carbonate, calcium citrate and a placebo was assessed in 10 healthy human subjects. Each subject was studied on five separate test days: fast, placebo, calcium acetate, calcium carbonate and calcium citrate. Net calcium absorption was measured by a method described in detail and validated previously. Bo-Linn, G. W. et al., *Journal of Clinical Investigation*, 73: 640-647 (1984). The procedure followed for this comparison is described below.

Subjects were prepared by a mannitol-electrolyte gastrointestinal lavage, in order to cleanse the gastrointestinal tract. Four hours after completion of the washout, subjects consumed 25 meq. of calcium or a placebo (lactose) with 100 ml of deionized water. On one of the test days (the fast day), subjects ingested no meal, placebo or calcium salt; the rest of the procedure was the same.

The subjects ate a test meal of 80 gm ground sirloin steak, 100 gm french fried potatoes, 30 gm Swiss cheese and 250 ml. water containing 10 gm of polyethylene glycol (PEG) as a nonabsorbable marker.

After each meal, subjects consumed 25 meq. of calcium, in the same form as had been consumed prior to the meal, or additional placebo, with 100 ml. of water. Duplicate meals were prepared (one for consumption and one to be analyzed for calcium and phosphorus). The duplicate meals contained, on average, 345±4 mg. of phosphorus and 214±2 mg. of calcium.

On different test days, one of the three calcium salts was taken. Calcium acetate was administered as reagent grade calcium acetate monohydrate (J. T. Baker Chemical Co.), calcium carbonate as analytical grade calcium carbonate (Mallinckrodt, Inc.) and calcium citrate as purum, p.a. calcium citrate tetrahydrate (Fluka). The salt was given in gelatin capsules. The total dose was 50 mEq of calcium (500 mg elemental calcium), one half of the dose (25 mEq) taken just before the meal and the other half immediately after the meal. On one test day a placebo was taken instead of a calcium-containing compound. The order of testing was random.

Ten hours after a meal, a second lavage was begun, using the procedure described above. This removed unabsorbed material from the gut. All urine voided during the 10-hour period was collected and analyzed for phosphorus and calcium. Rectal effluent was collected, pooled with any stool passed during the 10-hour period and analyzed for phosphorus and calcium. Results of these studies are shown in Tables 2, 3 and 4. Absorption was calculated according to the following equation:

Net phosphorus (P) or calcium (Ca) absorption = P (or Ca) content of duplicate meal (+Ca ingested as Ca salt) − [Effluent P (or Ca) after placebo or Ca salt − Effluent P (or Ca) after fast].

TABLE 2

| | PHOSPHORUS ABSORPTION (mg) | | | | | | | | | | | |
|---|---|---|---|---|---|---|---|---|---|---|---|---|
| | Subject | | | | | | | | | | | |
| BINDER | 1 | 2 | 3 | 4 | 5 | 6 | 7 | 8 | 9 | 10 | Mean | S.D. |
| PLACEBO | | | | | | | | | | | | |
| Intake | 358 | 343 | 353 | 323 | 336 | 338 | 357 | 344 | 346 | 322 | 342 | 13 |
| Rectal Effluent | 170 | 114 | 186 | 147 | 116 | 105 | 151 | 159 | 194 | 123 | 147 | 31 |
| Absorption | 275 | 287 | 240 | 226 | 284 | 285 | 266 | 281 | 206 | 284 | 263 | 29 |
| % Absorbed | 77 | 84 | 68 | 70 | 85 | 84 | 75 | 82 | 60 | 88 | 77 | 0.09 |
| CALCIUM ACETATE | | | | | | | | | | | | |
| Intake | 340 | 353 | 358 | 325 | 345 | 340 | 362 | 347 | 324 | 352 | 345 | 13 |
| Rectal Effluent | 271 | 359 | 386 | 346 | 223 | 318 | 306 | 355 | 353 | 320 | 324 | 48 |
| Absorption | 156 | 52 | 45 | 29 | 186 | 74 | 116 | 88 | 25 | 117 | 89 | 54 |
| % Absorbed | 46 | 15 | 13 | 9 | 54 | 22 | 32 | 25 | 8 | 33 | 26 | 0.16 |
| % BND | 31 | 69 | 55 | 61 | 31 | 63 | 42 | 56 | 52 | 55 | 52 | 0.13 |
| CALCIUM CARBONATE | | | | | | | | | | | | |
| Intake | 344 | 352 | 328 | 319 | 360 | 339 | 352 | 345 | 366 | 363 | 347 | 15 |
| Rectal Effluent | 187 | 272 | 285 | 271 | 266 | 243 | 280 | 288 | 296 | 245 | 263 | 32 |
| Absorption | 244 | 138 | 116 | 98 | 158 | 148 | 132 | 153 | 124 | 203 | 151 | 43 |
| % Absorbed | 71 | 39 | 35 | 31 | 44 | 44 | 38 | 44 | 34 | 56 | 44 | 0.12 |
| % BND | 6 | 44 | 33 | 39 | 41 | 41 | 37 | 37 | 26 | 32 | 34 | 0.11 |
| CALCIUM CITRATE | | | | | | | | | | | | |
| Intake | 346 | 346 | 319 | 354 | 322 | 362 | 345 | 345 | 352 | .359 | 345 | 14 |
| Rectal Effluent | 228 | 225 | 268 | 254 | 176 | 232 | 270 | 285 | 290 | 194 | 242 | 38 |
| Absorption | 205 | 179 | 124 | 150 | 210 | 182 | 135 | 156 | 116 | 250 | 171 | 43 |
| % Absorbed | 59 | 52 | 39 | 42 | 65 | 50 | 39 | 45 | 33 | 70 | 49 | 0.12 |
| % BND | 18 | 32 | 29 | 28 | 19 | 34 | 35 | 36 | 27 | 19 | 28 | 0.07 |

Fasting level = 67 ± 16

TABLE 3

| | CALCIUM ABSORPTION (mg) | | | | | | | | | | | |
|---|---|---|---|---|---|---|---|---|---|---|---|---|
| | Subject | | | | | | | | | | | |
| BINDER | 1 | 2 | 3 | 4 | 5 | 6 | 7 | 8 | 9 | 10 | Mean | S.D. |
| PLACEBO | | | | | | | | | | | | |
| Intake | 200 | 219 | 215 | 211 | 214 | 208 | 215 | 217 | 221 | 217 | 214 | 6 |
| Rectal Effluent | 226 | 181 | 225 | 212 | 262 | 189 | 154 | 153 | 297 | 193 | 209 | 46 |
| Absorption | −3 | 66 | 28 | 36 | −34 | 64 | 76 | 134 | −28 | 75 | 37 | 18 |
| % Absorbed | −2 | 30 | 13 | 17 | −16 | 31 | 35 | 63 | −13 | 35 | 19 | 0.24 |
| CALCIUM | | | | | | | | | | | | |

TABLE 3-continued

CALCIUM ABSORPTION (mg)

| BINDER | 1 | 2 | 3 | 4 | Subject 5 | 6 | 7 | 8 | 9 | 10 | Mean | S.D. |
|---|---|---|---|---|---|---|---|---|---|---|---|---|
| ACETATE | | | | | | | | | | | | |
| Intake | 1235 | 1209 | 1272 | 1235 | 1232 | 1182 | 1142 | 1247 | 1255 | 1221 | 1223 | 38 |
| Rectal Effluent | 1002 | 1028 | 1133 | 1109 | 1191 | 1014 | 956 | 1138 | 1094 | 1035 | 1070 | 74 |
| Absorption | 256 | 209 | 177 | 163 | 55 | 213 | 201 | 182 | 209 | 237 | 190 | 55 |
| % Absorbed | 21 | 17 | 14 | 13 | 4 | 18 | 18 | 15 | 17 | 19 | 16 | 0.05 |
| CALCIUM CARBONATE | | | | | | | | | | | | |
| Intake | 1203 | 1213 | 1201 | 1199 | 1215 | 1190 | 1199 | 1181 | 1220 | 1203 | 1202 | 12 |
| Rectal Effluent | 922 | 474 | 901 | 1021 | 1052 | 992 | 1139 | 1015 | 1020 | 876 | 941 | 182 |
| Absorption | 304 | 767 | 338 | 215 | 177 | 243 | 75 | 239 | 248 | 378 | 298 | 185 |
| % Absorbed 25 | 63 | 23 | 18 | 15 | 20 | 6 | 20 | 20 | 31 | 25 | 0.15 | |
| CALCIUM CITRATE | | | | | | | | | | | | |
| Intake | 1183 | 1191 | 1187 | 1201 | 1178 | 1194 | 1158 | 1253 | 1205 | 1222 | 1197 | 26 |
| Rectal Effluent | 969 | 910 | 1080 | 1076 | 899 | 1002 | 1061 | 942 | 768 | 971 | 97 | |
| Absorption | 237 | 309 | 145 | 232 | 116 | 340 | 171 | 265 | 311 | 505 | 263 | 113 |
| % Absorbed | 20 | 26 | 12 | 19 | 10 | 28 | 15 | 21 | 26 | 41 | 22 | 0.09 |

Fasting level = 37 ± 18

TABLE 4

URINE PHOSPHORUS (mg)

| | 1 | 2 | 3 | 4 | 5 | 6 | 7 | 8 | 9 | 10 | Mean | S.D. |
|---|---|---|---|---|---|---|---|---|---|---|---|---|
| Placebo | 593 | 278 | 337 | 376 | 520 | 309 | 631 | 298 | 421 | 398 | 416 | 125 |
| Calcium Acetate | 507 | 63 | 324 | 267 | 300 | 129 | 429 | 169 | 146 | 115 | 245 | 146 |
| Calcium Carbonate | 205 | 334 | 293 | 424 | 334 | 415 | 559 | 235 | 151 | 205 | 316 | 125 |
| Calcium Citrate | 602 | 359 | 253 | 348 | 318 | 388 | 419 | 118 | 457 | 239 | 350 | 132 |

Fasting level = 327 ± 147

The results demonstrate that calcium acetate results in the inhibition of phosphorus absorption and that calcium acetate is a more effective phosphorus binder (results in greater inhibition of phosphorus absorption) than either calcium carbonate or calcium citrate. In addition, they demonstrate that calcium acetate is a more efficient inhibitor of calcium absorption, when ingested close in time to food and beverage consumption, than either calcium carbonate or calcium citrate.

The data shows that when used as a phosphorus binder, calcium acetate is a more effective phosphorus binder, resulting in less phosphorus absorption than either calcium carbonate or calcium citrate. In addition, use of calcium acetate results in less absorption of the ingested dose of calcium since the calcium is complexed with phosphorus as an insoluble, unabsorbable salt in the intestine. The insoluble calcium phosphate salt is eliminated with the stool. Secondary confirmation of this result is demonstrated by the urine phosphorus content results, which show that calcium acetate significantly ($p \leq 0.001$) reduces phosphate absorption, and ultimately phosphate available for excretion in the urine of these normal test subjects.

I claim:

1. A method for inhibiting gastrointestinal absorption of phosphorous in an individual, comprising:
   orally ingesting a quantity of calcium acetate sufficient to bind with phosphorous in the gastrointestinal tract.

2. The method according to claim 1 wherein the calcium acetate is present in an amount sufficient to provide between 10 to 200 milliequivalents of calcium.

3. The method according to claim 1 wherein the calcium acetate is in tablet form.

4. The method according to claim 1 wherein the calcium acetate is in gelatin capsule form.

5. A method for inhibiting gastrointestinal absorption of phosphorous in an individual, comprising:
   orally ingesting a quantity of calcium acetate at mealtimes.

6. The method according to claim 5 wherein the quantity of calcium acetate is present in an amount sufficient to produce between 10–200 milliequivalents of calcium.

7. The method according to claim 5 wherein the quantity of calcium acetate is in tablet form.

8. The method according to claim 5 wherein the quantity of calcium acetate is in gelatin capsule form.

* * * * *

REEXAMINATION CERTIFICATE (3457th)
United States Patent [19]
Fordtran

[11] B1 4,870,105
[45] Certificate Issued Mar. 10, 1998

[54] PHOSPHORUS BINDER

[75] Inventor: John S. Fordtran, Dallas, Tex.

[73] Assignee: Braintree Laboratories, Inc., Braintree, Mass.

Reexamination Request:
No. 90/004,483, Dec. 13, 1996

Reexamination Certificate for:
Patent No.: 4,870,105
Issued: Sep. 26, 1989
Appl. No.: 35,341
Filed: Apr. 7, 1987

[51] Int. Cl.$^6$ .......................... A61K 31/19; A61K 47/00
[52] U.S. Cl. ............................................ 514/557; 514/784
[58] Field of Search .................................. 514/557, 784

[56] References Cited

FOREIGN PATENT DOCUMENTS 61-36222  2/1986  Japan .

OTHER PUBLICATIONS

Goodman & Gilman, *The Pharmacological Basis of Therapeutics*, 5th Ed., MacMillan, 1975.
Lewis, Richard J., *Hawley's Condensed Chemical Dictionary*, 12th Ed., Van Nostrand Reinhold, 1993, p. 908.
*Dorland's Illustrated Medical Dictionary*, 26th Ed., W.B. Saunders Company, 1985.

*Chemical Abstracts*, vol. 52, Col. 3277a (1958).

*Chemical Abstracts*, vol. 57, Col. 1297c (1962).

*Chemical Abstracts*, vol. 57, Col. 3277c (1962).

Cushner et al., "Calcium Citrate, A New Phosphate–Binding and Alkalinizing Agent For Patients With Renal Failure", *Current Therapeutic Research*, vol. 40, No. 6, Dec., 1986.

Addison et al., "Calcium Carbonate: An Effective Phosphorus Binder in Patients With Chronic Renal Failure", *Current Therapeutic Research*, vol. 38, No. 2, Aug., 1985.

Fournier et al., "Calcium Carbonate, An Aluminum—Free Agent for Control of Hyperphosphatemia, Hypocalcemia and Hyperparathyroidism in Uremia", *Kidney International*, vol. 20, Suppl. 18 (Feb., 1986), pp. S–114–S–119.

*Primary Examiner*—Kevin E. Weddington

[57] ABSTRACT

A composition for oral administration to an individual for the purpose of inhibiting gastrointestinal absorption of phosphorous, which includes calcium acetate. A method of inhibiting gastrointestinal absorption of phosphorous, comprising administering orally the composition, preferably close in time to food and beverage consumption.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *